(12) United States Patent
El-Said

(10) Patent No.: US 11,540,924 B1
(45) Date of Patent: Jan. 3, 2023

(54) REMOTELY ADJUSTABLE ORTHOPEDIC PROSTHESES

(71) Applicant: Ezat El-Said, Orlando, FL (US)

(72) Inventor: Ezat El-Said, Orlando, FL (US)

(*) Notice: Subject to any disclaimer, the term of this patent is extended or adjusted under 35 U.S.C. 154(b) by 0 days.

(21) Appl. No.: 17/823,012

(22) Filed: Aug. 29, 2022

Related U.S. Application Data

(60) Provisional application No. 63/267,982, filed on Feb. 14, 2022.

(51) Int. Cl.
*A61F 2/36* (2006.01)
*A61F 2/30* (2006.01)

(52) U.S. Cl.
CPC .......... *A61F 2/3609* (2013.01); *A61F 2/3662* (2013.01); *A61F 2002/30332* (2013.01); *A61F 2002/30405* (2013.01); *A61F 2002/30537* (2013.01); *A61F 2002/365* (2013.01)

(58) Field of Classification Search
None
See application file for complete search history.

(56) References Cited

U.S. PATENT DOCUMENTS

| | | | |
|---|---|---|---|
| 8,734,488 B2* | 5/2014 | Pool | A61B 17/707 606/259 |
| 2006/0004459 A1 | 1/2006 | Hazebrouck et al. | |
| 2013/0204376 A1 | 8/2013 | Disilvestro et al. | |
| 2018/0064542 A1 | 3/2018 | Knöchel | |
| 2018/0271664 A1 | 9/2018 | Hermle | |
| 2019/0015138 A1* | 1/2019 | Schwardt | A61B 17/62 |

FOREIGN PATENT DOCUMENTS

DE 102005045070 A1 4/2007

* cited by examiner

*Primary Examiner* — Megan Y Wolf
(74) *Attorney, Agent, or Firm* — Fortem IP LLP

(57) ABSTRACT

An adjustable orthopedic implant can include a neck assembly, a stem assembly, and a drive assembly having a first portion coupled to the neck assembly and a second portion coupled to the stem assembly. The drive assembly can include an actuator configured to rotate in response to the actuation signal, and a threaded rod coupled to the actuator and configured to rotate in response to rotation of the actuator. The threaded rod can engage a threaded receptacle of the stem assembly such that rotation of the threaded rod in a first direction urges the neck assembly and the stem assembly closer together, and rotation of the threaded rod in a second, opposite direction urges the neck assembly and the stem assembly further apart.

16 Claims, 18 Drawing Sheets

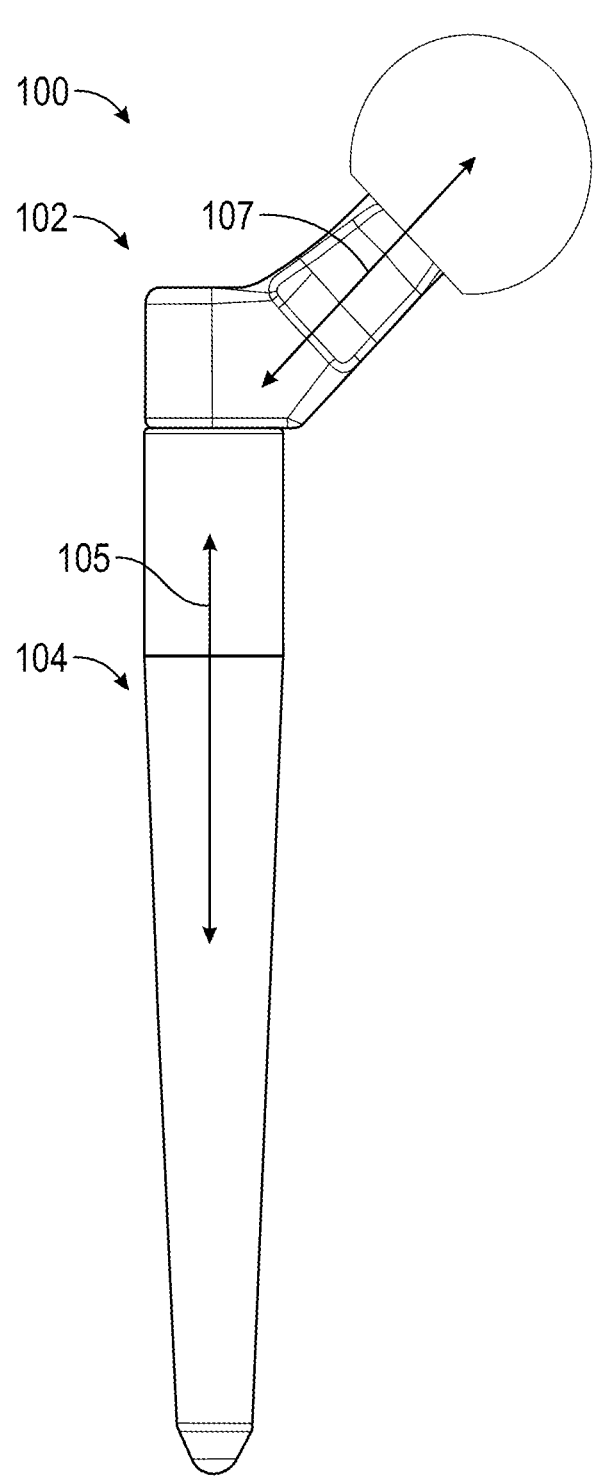
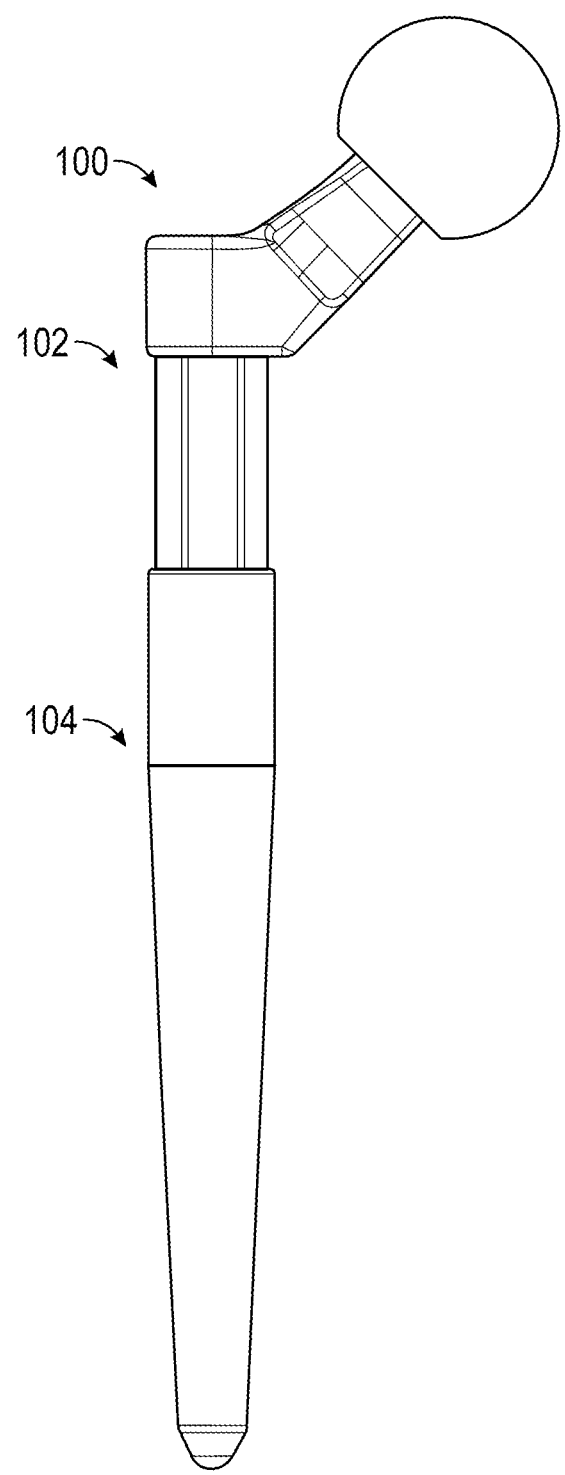
FIG. 1A  FIG. 1B

REMOTELY ADJUSTABLE ORTHOPEDIC PROSTHESES

CROSS-REFERENCE TO RELATED APPLICATIONS

This application claims priority to U.S. Provisional Application No. 63/267,982, filed Feb. 14, 2022, which is hereby incorporated by reference in its entirety.

TECHNICAL FIELD

The present technology generally relates to orthopedic prostheses, and in particular, to remotely adjustable orthopedic prosthesis such as artificial joint implants.

BACKGROUND

Orthopedic implants are often used to treat patients with bone fractures or other conditions that require stabilization, as well as for partial or total joint arthroplasty procedures. Examples include hip joint implants, shoulder joint implants, and knee joint implants, which often include an elongated stem portion configured to be inserted into a patient's medullary cavity (e.g., of the femur in the case of hip implants, of the humerus in the case of shoulder implants, and of the tibia in the case of knee implants) and a neck portion that is coupled to the stem portion and includes a rod configured to receive a semispherical member that serves as the artificial joint head. Following implantation of the implant, the artificial joint head engages with the patient's existing joint socket (or alternatively a prosthetic joint socket in the case of total joint arthroplasty).

Typically, implants are selected for a particular patient based on measurements of the patient's anatomy prior to surgery. However, it can be challenging to ensure that the implant is appropriately dimensioned for the particular patient, especially as the final placement of the implant may not be accurately determined prior to surgery. As a result, in some instances a patient may have a limb length discrepancy (LLD) following such procedures, in which the limb in which the implant has been inserted is either shorter or longer than the opposing limb.

Unfortunately, LLD is a common complication resulting from hip implants. When standing with the weight equally distributed on both legs, patients with LLD have their pelvis and sacrum tilted to the side of the short leg, resulting in relative deterioration of femoral head containment and lateral flexion of the spine. The debilitative effects lead to muscle spasms, muscular pain, and weakness in the shorter limb, nerve injury from mechanical stress of a lengthened limb can lead to an overall loss in motility. This also raises concerns that LLD in growing children could promote the development of hip dysplasia and/or scoliosis; further complications include hip, knee, and lumbar arthritis. While there are surgical techniques to reduce the risk of LLD, this condition is still reported to occur in a high proportion of patients. Current therapies to alleviate LLD include shoe lifts to equalize limb length, physical therapy, and gait training. Despite these therapeutic approaches, the subsequent need for revision surgery is generally required, which can incur significant cost.

LLD may also be the result of congenital disorders, rather than as a result of an orthopedic implant. For example, children born with malignant bone tumors may have a portion of the bone removed in their youth. As the child ages, the residual bone that has had a portion removed may not grow as quickly as the corresponding bone, resulting in a limb length discrepancy over time. In certain cases, children are born with idiopathic LLD that is not the result of any surgical intervention.

Accordingly, there remains a need for improved prosthetic implants that can be adjusted following surgical implantation.

BRIEF DESCRIPTION OF THE DRAWINGS

To easily identify the discussion of any particular element or act, the most significant digit or digits in a reference number refer to the figure number in which that element is first introduced.

FIG. 1A illustrates a side view of an orthopedic implant in a longitudinally contracted state in accordance with one embodiment.

FIG. 1B illustrates the orthopedic implant of FIG. 1A in a longitudinally extended state accordance with one embodiment.

DETAILED DESCRIPTION

Figure 1C:
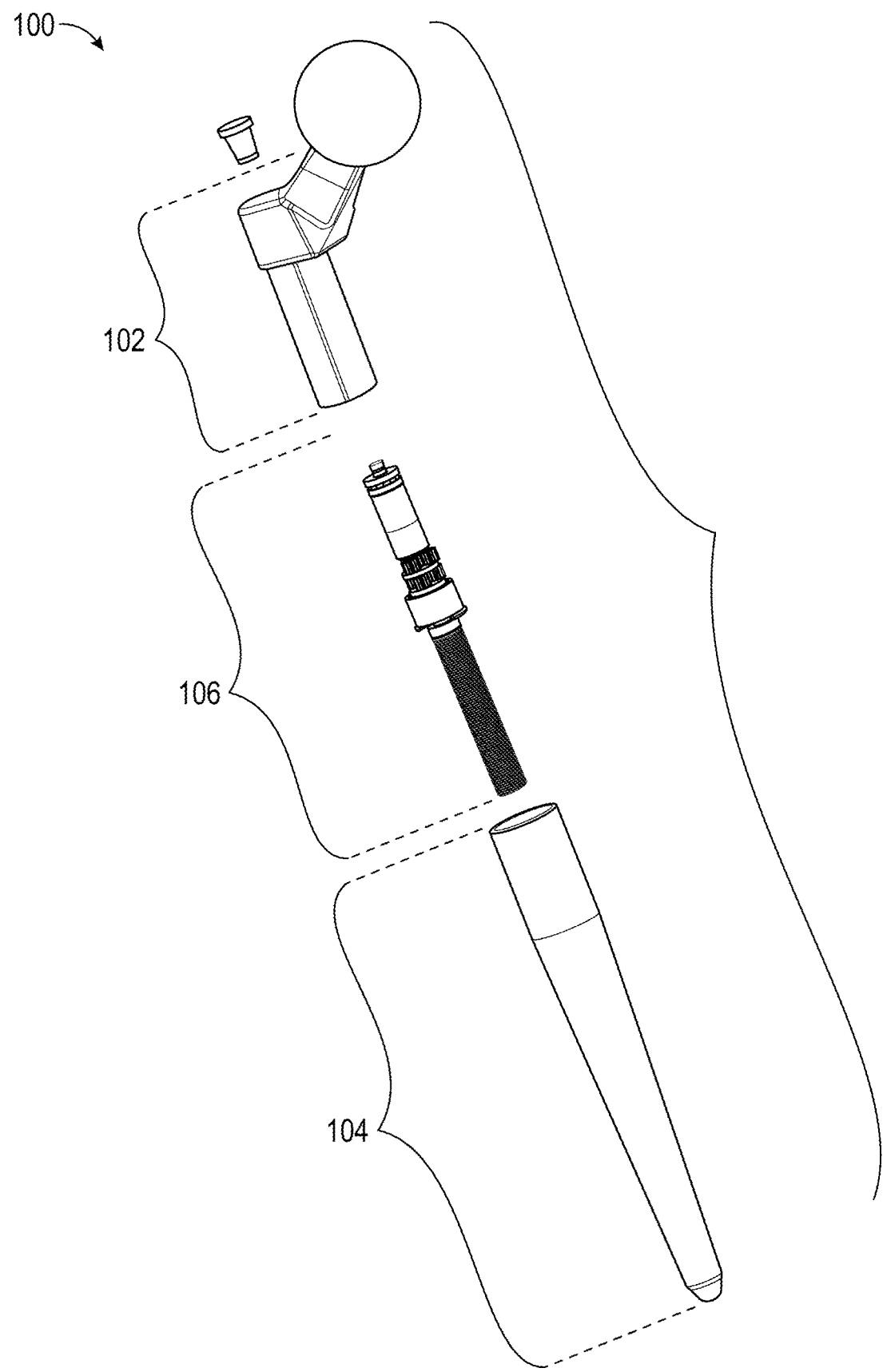
FIG. 1C illustrates is a partially exploded perspective view of the orthopedic implant shown in FIG. 1A and FIG. 1B.

The present technology relates to remotely adjustable orthopedic prosthetics. Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The headings provided herein are for convenience only and do not interpret the scope or meaning of the claimed present technology. Embodiments under any one heading may be used in conjunction with embodiments under any other heading.

As noted above, conventional orthopedic implants have a fixed length and as such cannot be adjusted following implantation. In some instances, this can lead to limb length discrepancies following surgery. Particularly in the case of hip implants, such limb length discrepancies can reduce patient mobility, introduce gait problems, and hinder successful recover. To address these and other problems, the present technology relates to a modular and adjustable hip (or shoulder or other suitable joint) implant that includes a neck portion (e.g., including a ball configured to engage the socket of the pelvis) and a stem portion (e.g., configured to be inserted into the medullary cavity of the femur). A threaded rod can be threadably inserted into the stem portion with an upper segment of the threaded rod protruding from the stem portion. This upper portion of the threaded rod can mate with the stem portion via a latching mechanism. Once mated together, the neck portion can be actuated to cause the threaded rod to rotate relative to the stem portion, thereby either lengthening the implant (moving the ends of the stem portion and the neck portion further apart) or shortening the implant (moving the ends of the stem portion and the neck portion closer together).

These adjustments via rotation of the threaded rod can be actuated remotely (i.e., without direct physical contact between a control device and the implant). For example, a magnet within the neck portion can be configured to rotate in the presence of an external magnetic field (e.g., using an external controller device held up against the patient's hip). This rotation of the internal magnet causes an internal gearbox to rotate, thereby rotating the threaded screw and moving the neck portion and the stem portion either further apart (lengthening the implant) or closer together (shortening the implant).

The modular construction allows a surgeon to easily change between different sized necks and/or stems, and also allows for the stem to be hammered into place within the medullary canal without risking damage to the more sensitive gear and magnetic components disposed within the neck portion.

At least the outer casing of the implant (both the stem and neck portions) may be 3D printed, for example using titanium or other biocompatible structure and formed in a porous configuration to promote bone ingrowth following implantation. Some or all of the components within the implant can be made of ceramic, which may be useful to avoid metal-on-metal interactions. Inflammatory reactions to metal particles in soft tissues are a well-known consequence of metal-on-metal hip arthroplasty. These reactions, known as inflammatory pseudotumor, aseptic lymphocytic vasculitis associated lesion (ALVAL), and metallosis, have been included under the umbrella term adverse reactions to metal debris (ARMD). The broad ARMD spectrum ranges from asymptomatic microscopic cysts to massive soft tissue tumors (pseudotumors). Therefore, for any metal-on-metal components, it may be beneficial to choose one to be the titanium material (or other biocompatible metal) and the other to be a ceramic material.

The magnetic components described herein (e.g., an internal magnet within the drive assembly) can be made of metallic material (e.g., ceramic, neodymium, etc.) and may optionally be coated with a biocompatible material such as polyurethane to prevent corrosion and potentially adverse effects within the body.

In various examples, the implant can be inserted and secured in place using press-fit fixation with or without additional fixation components such as fixation screws, bone cement, etc.

Although several examples described below relate to an implant in which the stem can be elongated or shortened, in various implementations a length of the neck portion of the implant can additionally or alternatively be adjustable. For example, the neck portion can include two components that are threadably mated together (e.g., an outer component on which the ball can be mounted, and an inner component configured to mate with the stem portion), and these two components can be moveable relative to one another using a remotely actuatable mechanism as described elsewhere herein. In some examples, an implant can be adjustable both along its stem portion and along its neck portion, while in some instances an implant may be adjustable only the neck portion or only the stem portion.

In some embodiments, an adjustable orthopedic implant can be equipped with one or more integrated sensors, which can optionally communicate (e.g., via a wireless transceiver using WiFi, Bluetooth, NFC, or other communications protocol) with one or more external computing devices to provide information about the state of the implant while implanted within the patient's body. Example sensors can include, for example, mechanical sensors (e.g., sensing pressure, strain, stress, etc.), electromagnetic sensors (e.g., to detect the presence and/or magnitude of a magnetic field), fluid sensors (e.g., to detect the presence of fluid within internal compartments of the implant), chemical sensors (e.g., to detect and characterize osseointegration between the implant and the surrounding bone), activity sensors (e.g., accelerometers, gyroscopes, pedometers, etc. to monitor a patient's recovery) or any other suitable sensors. In some examples, corresponding electronic components can be housed within the implant, such as a power source, wireless communication components, signal processing components, etc.

Figure 1D:
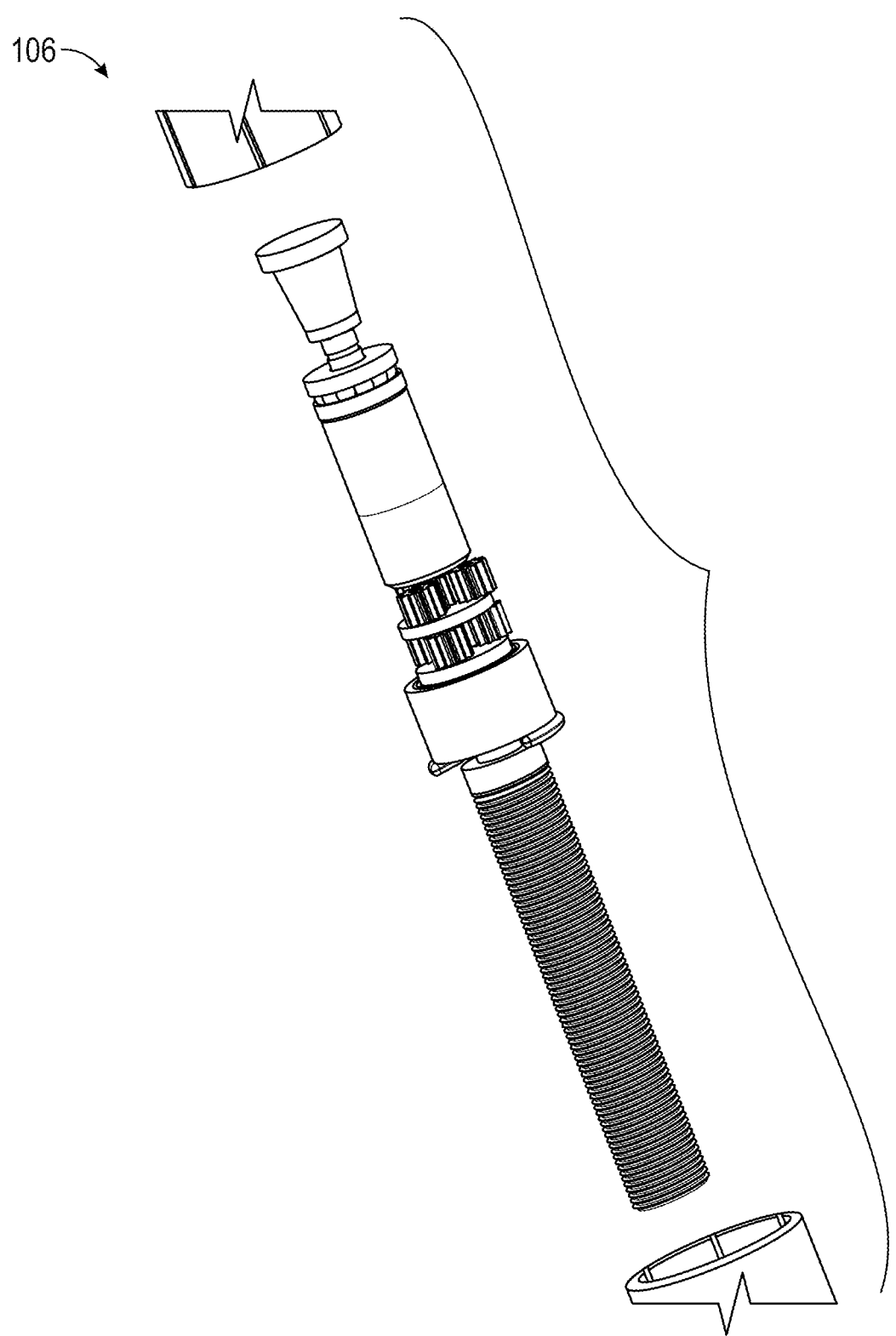
FIG. 1D illustrates enlarged detail view of a portion of the orthopedic implant shown in FIG. 1D.

FIG. 1A illustrates a side view of an orthopedic implant 100 in a longitudinally contracted state, and FIG. 1B illustrates the orthopedic implant 100 in a longitudinally extended state. FIG. 1C illustrates a partially exploded perspective view of the implant 100, and FIG. 1D shows an enlarged detail view of a portion of the implant 100 shown in FIG. 1C. As shown, the orthopedic implant 100 can include a first component such as a neck assembly 102 and a second component such as a stem assembly 104. The neck assembly and the stem assembly can be coupled together, and may be operably moved with respect to one another via a drive assembly 106 (FIG. 1C). As shown in FIG. 1A, the implant 100 can be adjusted along the long axis of the stem portion (indicated by arrow 105), for example via drive assembly 106. Additionally or alternatively, the implant 100 can be adjusted along the long axis of the neck portion (indicated by arrow 107), for example via a separate drive assembly (not shown) that can operate similarly to the drive assembly 106 described elsewhere herein.

In one example, the drive assembly 106 can be remotely actuated (e.g., via a wireless actuation signal delivered via an external control device) to move the implant towards a longitudinally contracted state (as shown in FIG. 1A) and/or towards a longitudinally extended state (as shown in FIG. 1B). In various embodiments, the implant may be positioned at any intermediate position between a fully contracted and fully extended state, such that any overall length of the implant within the maximum range of travel can be achieved.

As described in more detail below, in some embodiments the drive assembly 106 can include a threaded rod that threadably engages a threaded receptacle within the stem assembly 104. The drive assembly 106 can be configured to rotate the threaded rod in response to the actuation signal, thereby causing the threaded rod to rotate with respect to the threaded receptacle and urge the neck assembly 102 and the stem assembly 104 closer together or further apart (depending on the direction of rotation). The drive assembly 106 can include a permanent magnet configured to rotate in response to a magnetic field provided by an external control device. Additionally, in some embodiments the magnet is coupled to a gear assembly that is configured to step down rotational movement of the magnet into a lesser degree of rotation applied to the threaded rod.

Figure 2A:
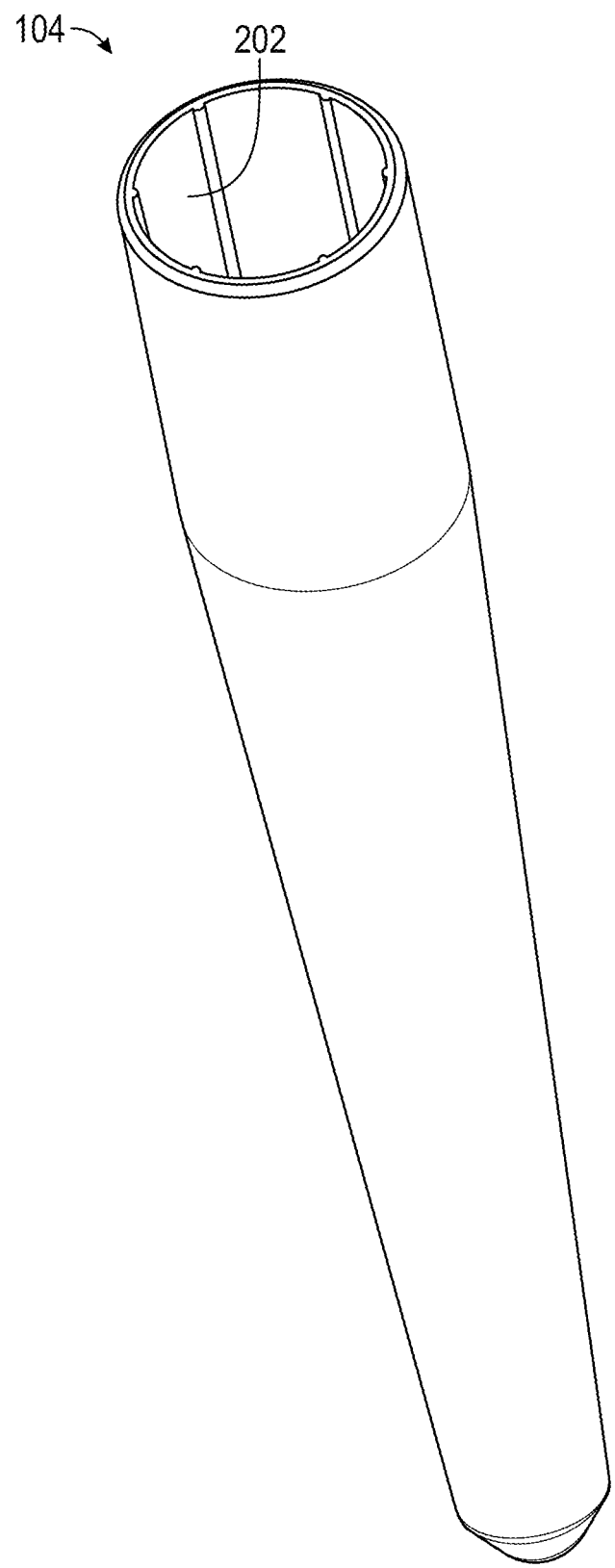
FIG. 2A illustrates a top perspective view of a stem assembly of an orthopedic implant in accordance with one embodiment.
Figure 2B:
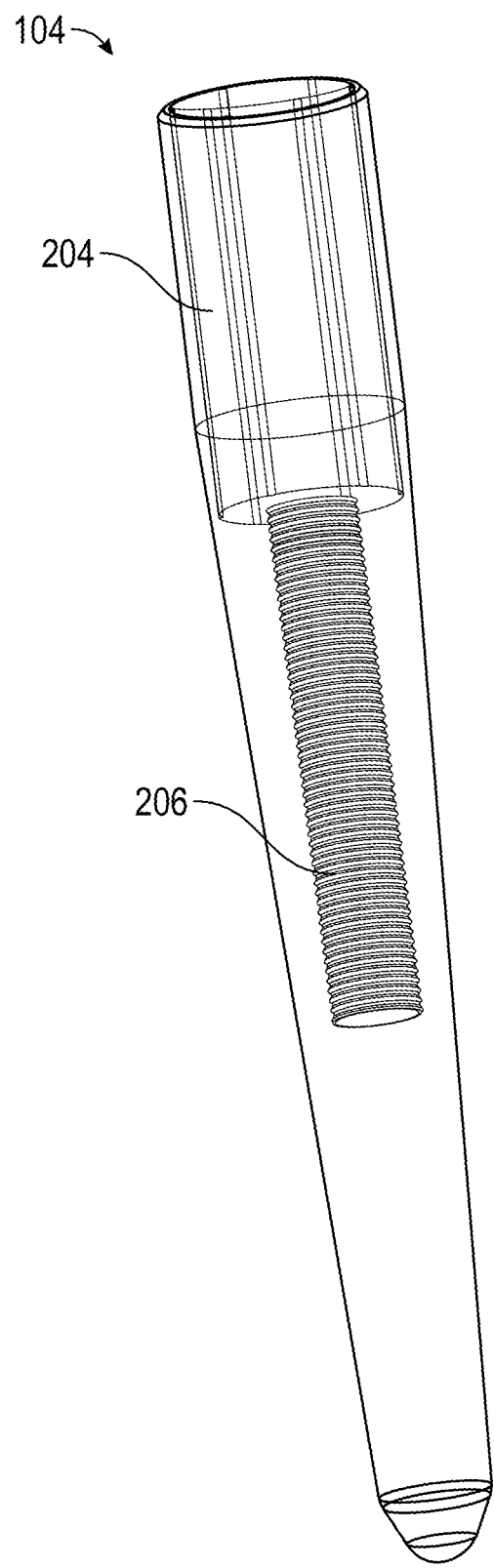
FIG. 2B illustrates a side transparent view of the stem assembly shown in FIG. 2B.

FIG. 2A illustrates a perspective side view of the stem assembly 104, and FIG. 2B illustrates a side view of the stem assembly 104 shown with partial transparency. Referring to FIG. 2A and FIG. 2B together, the stem assembly 104 can include an outer shell having an upper end configured to abut the neck assembly 102 and a lower opposite end having a reduced diameter (e.g., having a gradual taper in outer diameter toward the lower end). As will be understood by one of skill in the art, the stem assembly 104 can be sized and configured to be inserted (e.g., hammered) into a prepared medullary cavity of a patient's bone (e.g., a femur in the case of a hip implant). In various embodiments, the outer surface of the stem assembly 104 can be smooth or may have contours configured to increase engagement with the surrounding tissue (e.g., ridges, spikes, protrusions, etc.). In at least some embodiments, some or all of the stem assembly 104 can be formed with a porous structure to promote osseointegration. The stem assembly 104 also defines an interior chamber 202 configured to receive at least a portion of the drive assembly 106 therein. The interior chamber can include an upper portion 204 configured to receive a portion of the drive assembly 106, and a lower portion 206 that takes the form of a threaded receptacle configured to threadably engage the threaded rod of the drive assembly 106.

Figure 3B:
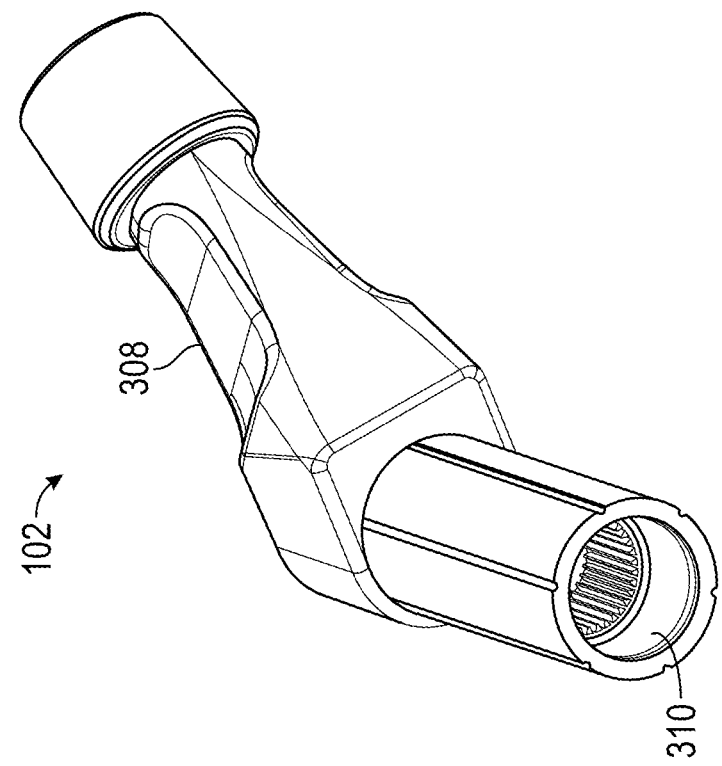
FIG. 3B illustrates a bottom perspective view of the neck assembly shown in FIG. 3A.
Figure 3A:
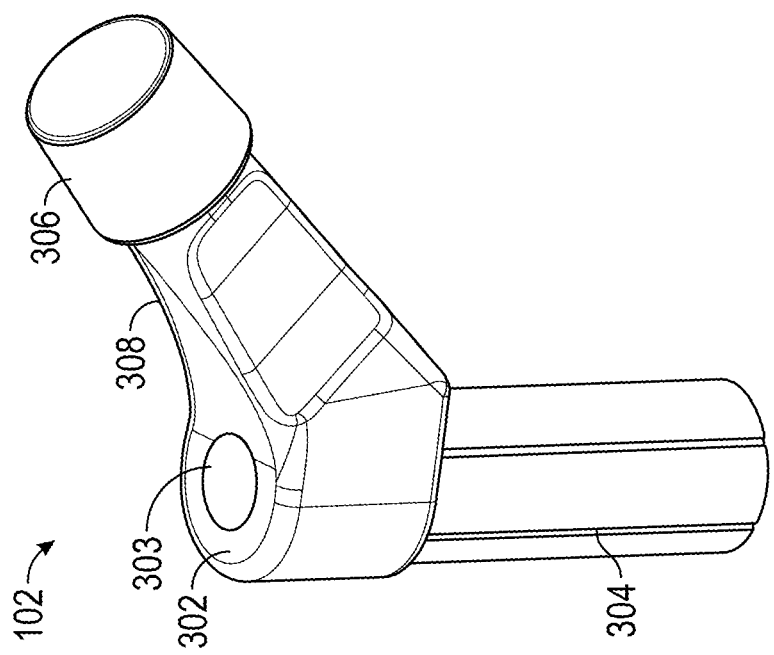
FIG. 3A illustrates a top perspective view of a neck assembly of an orthopedic implant in accordance with one embodiment.

FIG. 3A illustrates a perspective side view of the neck assembly 102, and FIG. 3B illustrates a bottom perspective view of the neck assembly 102 shown in FIG. 3A. With reference to FIG. 3A and FIG. 3B together, the neck assembly 102 can include a shoulder portion 302 having an upper surface, a downwardly extending shaft portion 304, and a neck portion 308 extending at an angle relative to the shaft portion 306. The particular orientation and lengths of the shaft portion 306, shoulder portion 302, and neck portion 308 can be selected based on the patient's particular anatomy and other suitable characteristics. In operation, the neck portion 308 can be sized and configured to receive thereover a prosthetic ball as part of a prosthetic joint. This prosthetic ball can be configured to abut the acetabular region of the joint, and functions to replace the patient's femoral head (or head of other suitable bone).

As illustrated, the shoulder portion 302 can include a receptacle in which a locking member 303 is received. As described in more detail below with respect to FIGS. 4A-5C, the locking member 303 can be a generally conical member that is received within the receptacle of the shoulder portion 302 and engages an upper portion of the drive assembly 106. In some implementations, the locking member 303 can be removed before or after the implant 100 has been assembled, thereby permitting access to at least some components of the drive assembly 106 (e.g., to make manual adjustments to the drive assembly 106, to lock the drive assembly 106 in position to preclude further adjustments, to manually elongate or shorten the implant 100, or to perform other operations).

As shown in FIG. 3B, the shaft portion 304 defines an interior cavity 310 configured to receive at least an upper portion of the drive assembly 106 therein. In various embodiments, the interior cavity 310 can include structural features configured to securely engage the drive assembly 106 such that at least a portion of the drive assembly 106 cannot rotate with respect to the cavity 310. Such structural features can include posts, ridges, protrusions, clasps, or any other suitable mechanism for limiting rotational movement of the drive assembly 106.

Figure 4A:
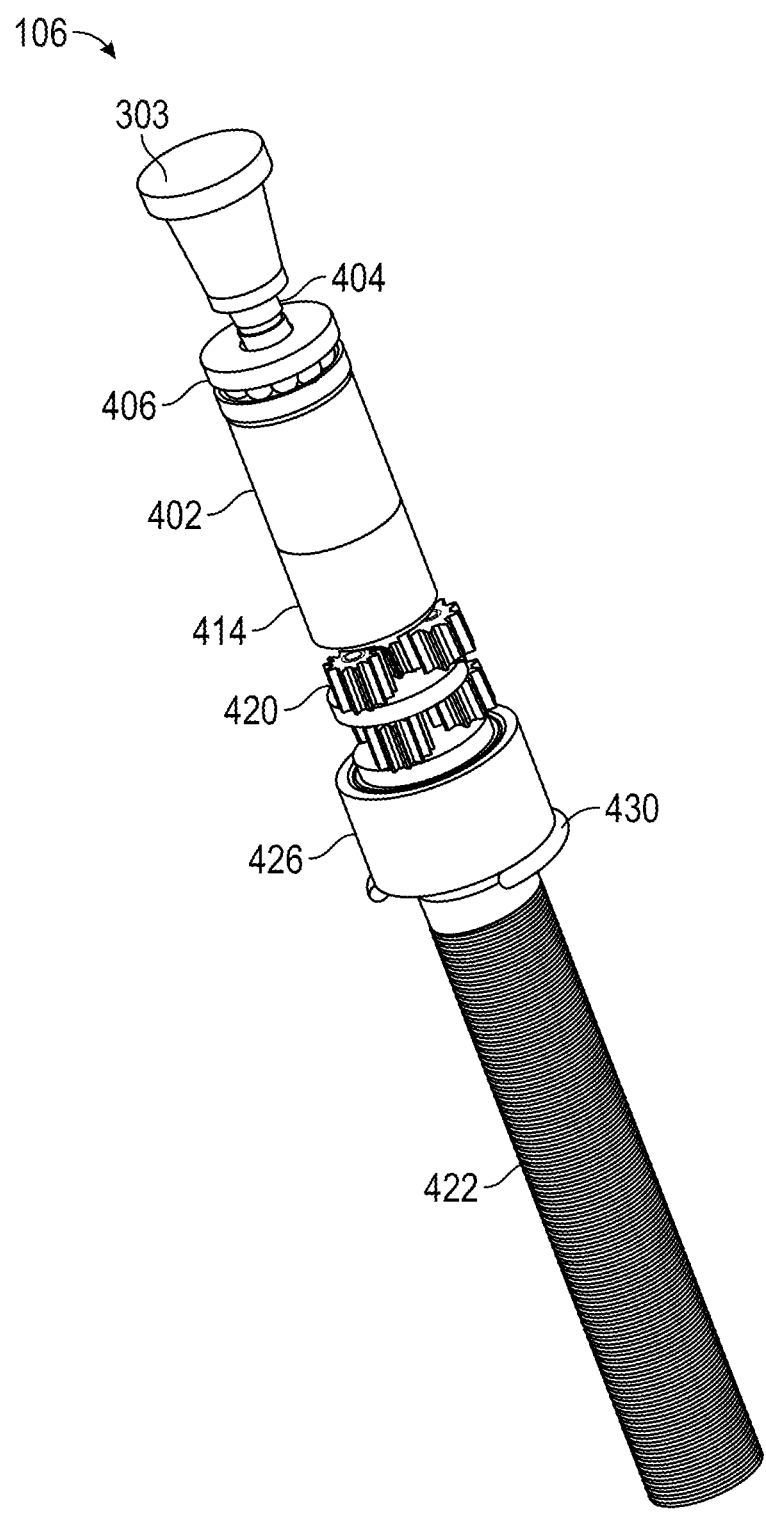
FIG. 4A illustrates an upper side perspective view of a drive assembly of an orthopedic implant in accordance with one embodiment.
Figure 4B:
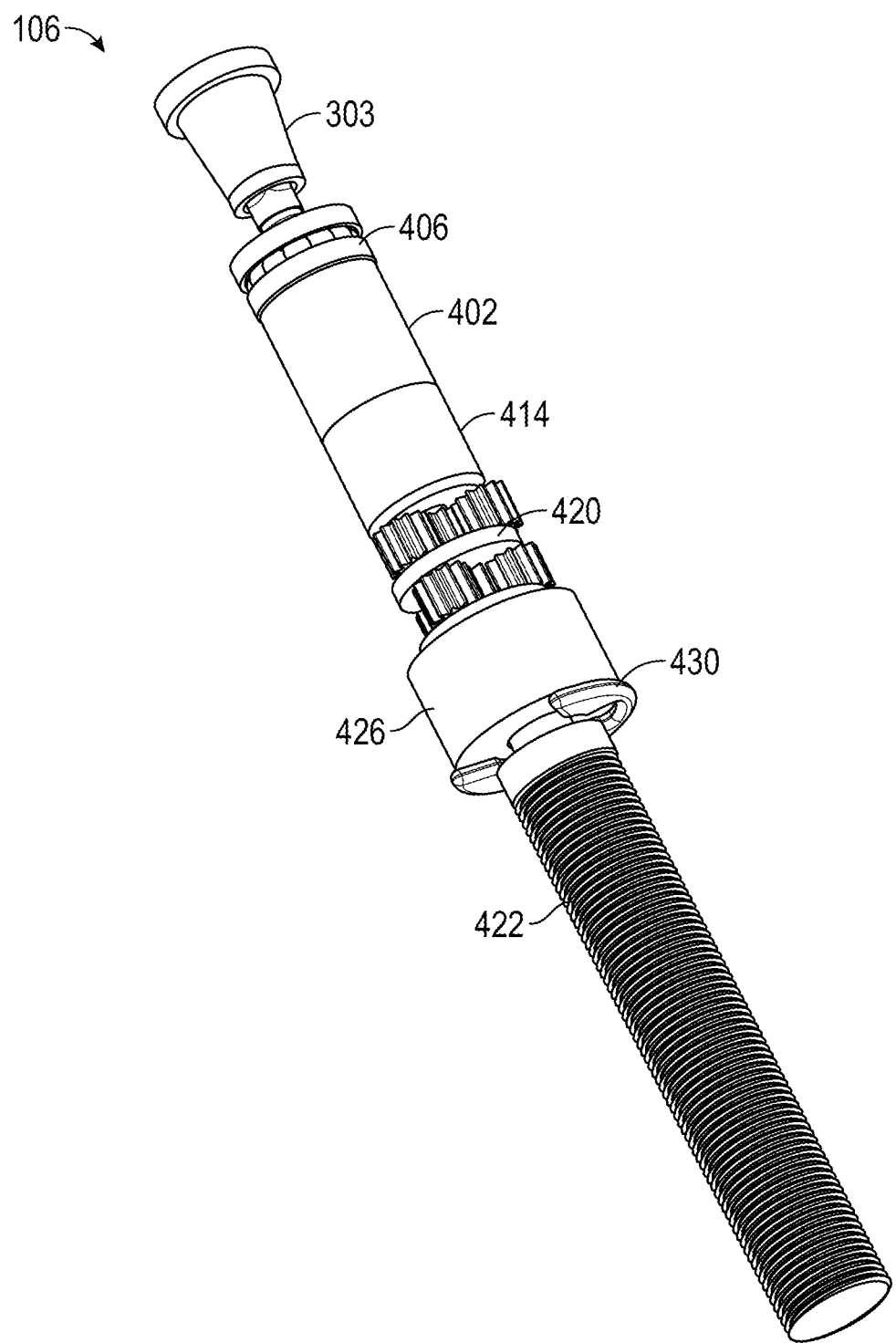
FIG. 4B illustrates a lower side perspective view of the drive assembly shown in FIG. 4A.
Figure 4C:
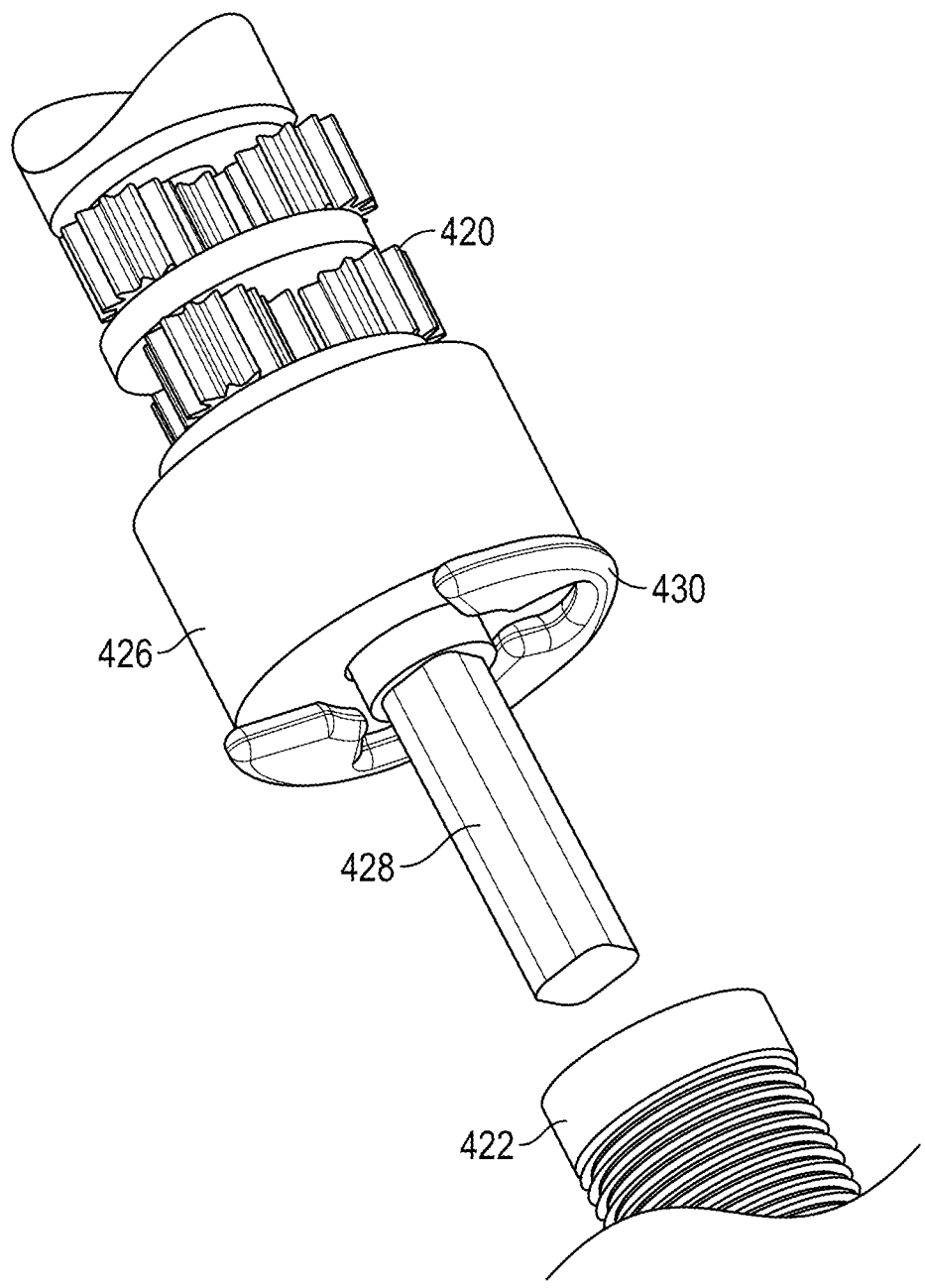
FIG. 4C illustrates an enlarged detail view of a portion of the drive assembly shown in FIG. 4B, with the threaded rod in a decoupled state.
Figure 4D:
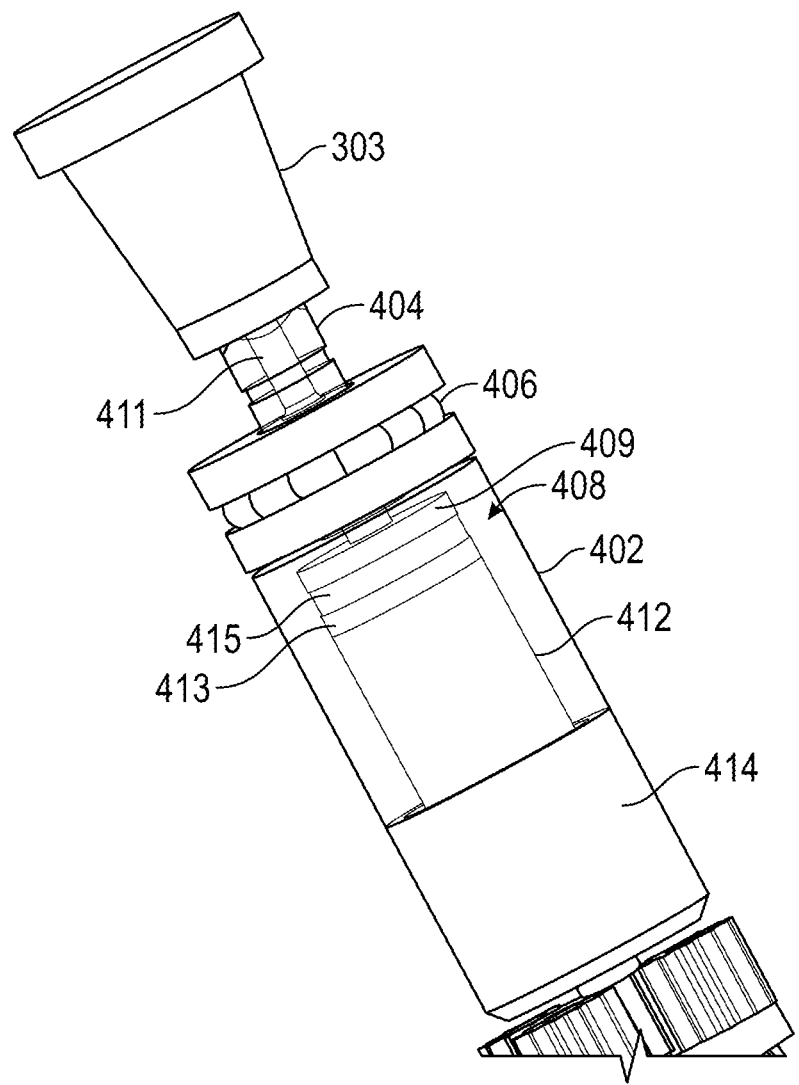
FIG. 4D illustrates an enlarged detail view of another portion of the drive assembly shown in FIG. 4B.
Figure 5A:
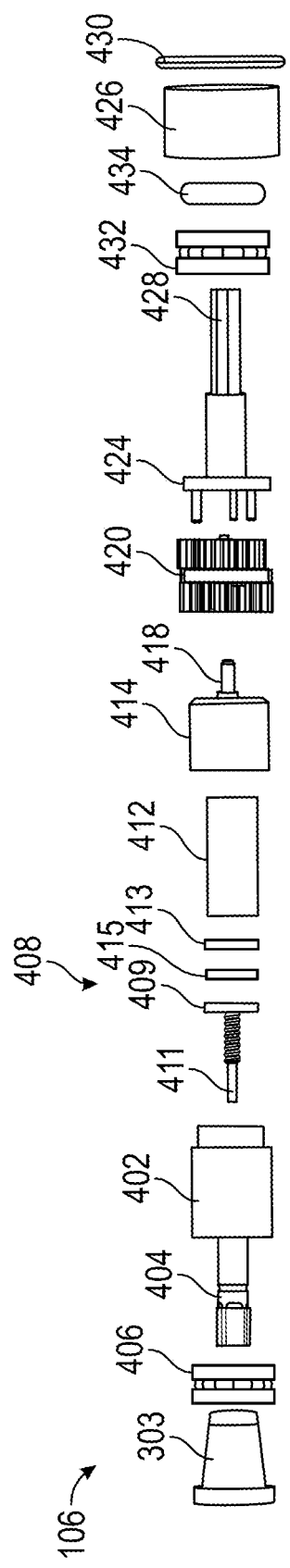
FIG. 5A illustrates an exploded view of the drive assembly of an orthopedic implant with certain components omitted for clarity.
Figure 5B:
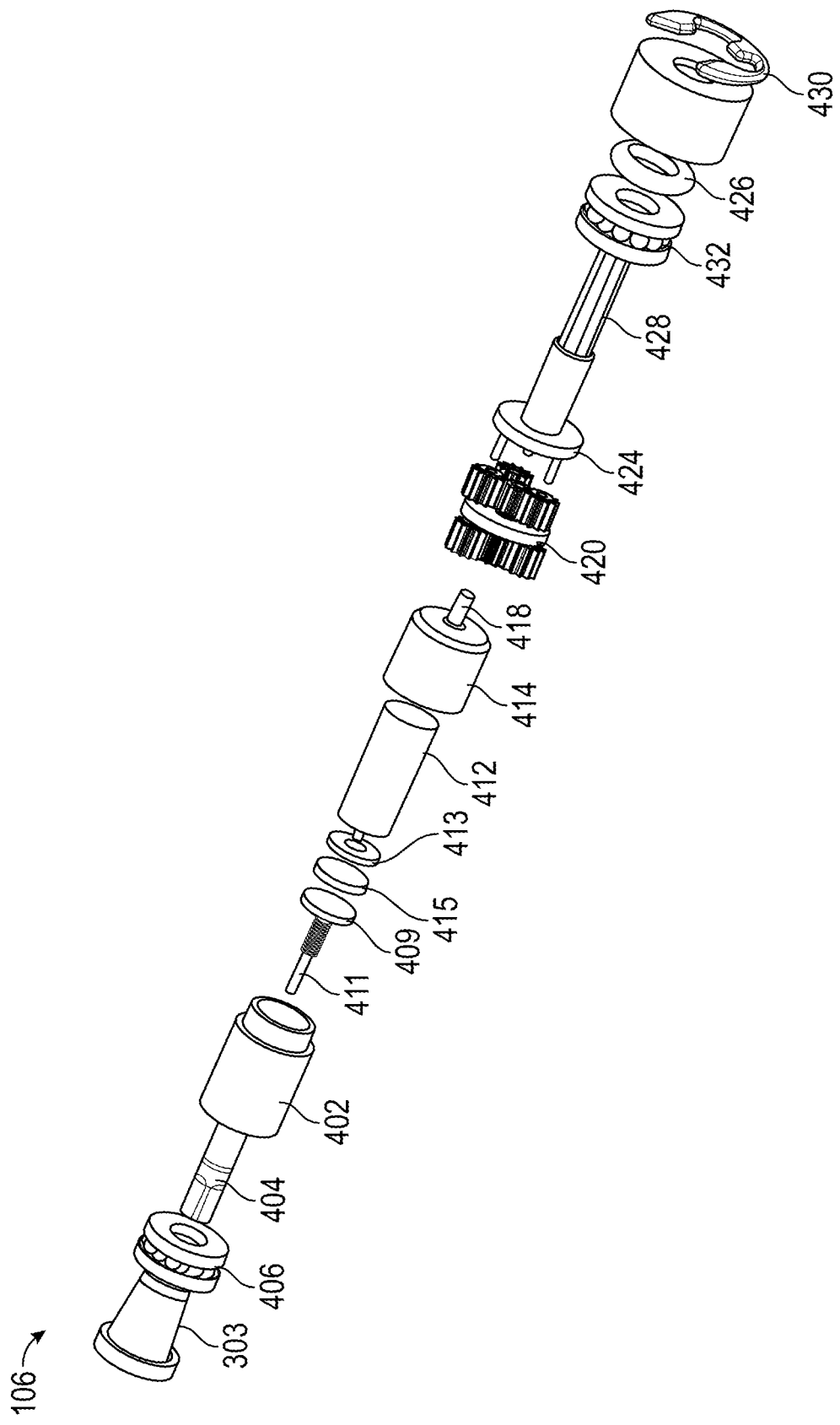
FIG. 5B illustrates a lower perspective view of the exploded drive assembly shown in FIG. 5A.
Figure 5C:
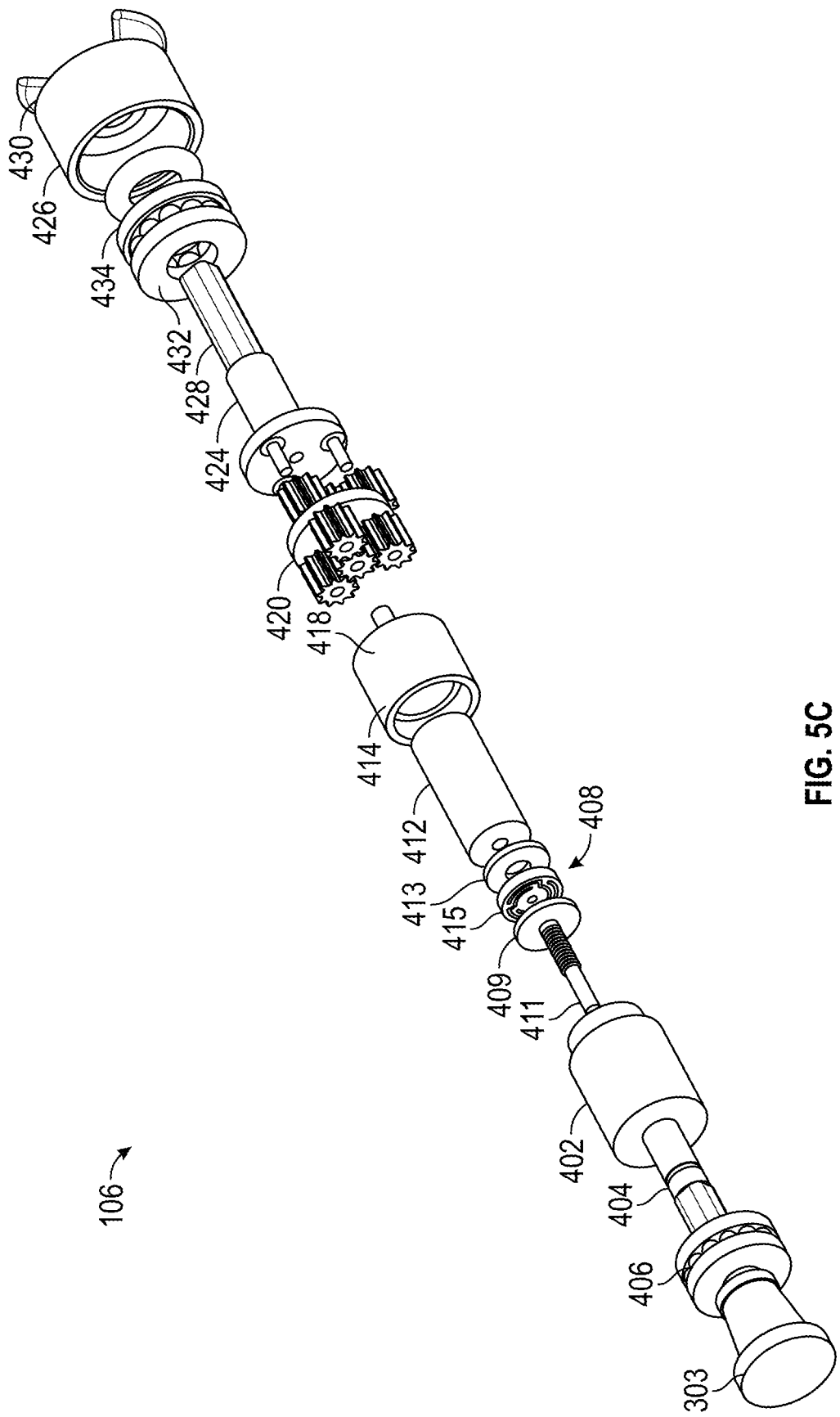
FIG. 5C illustrates an upper perspective view of the exploded drive assembly shown in FIG. 5A.

FIG. 4A illustrates a top perspective view of the drive assembly 106, FIG. 4B illustrates a bottom perspective view of the drive assembly 106, FIG. 4C illustrates an enlarged detail view of a portion of the drive assembly 106 with the threaded rod in a decoupled state, and FIG. 4D illustrates an enlarged detail view of a clutch mechanism 408 of the drive assembly 106. FIGS. 5A-5C illustrate exploded side, lower perspective, and upper perspective views, respectively, of the drive assembly 106 with certain components hidden for clarity. With reference to FIGS. 4A-5C together, the drive assembly 106 includes an upper housing 402 with an upwardly protruding rod 404 and a bearing 406 disposed thereon (e.g., circumferentially surrounding the rod). The rod 404 can define an inner lumen into which additional components are received, as described in more detail below. The locking member 303 is mounted over an uppermost end of the protruding rod 404. As noted above, the locking member 303 can have a generally cylindrical shape, with a planar upper surface configured to sit flush with an upper surface of the neck assembly (FIG. 3A). Although the illustrated locking member 303 mates with the neck assembly via a friction fit, in other implementations the locking member 303 can utilize a locking mechanism slot, pin mechanism, threaded engagement, or any other suitable technique for affixing the locking member 303 with respect to the neck assembly. In operation, this upper portion of the drive assembly 106 can be inserted into the cavity of the neck assembly and secured in position. A magnet 412 (FIGS. 5A-5C) can be disposed within the upper housing 402. The magnet 412 can take the form of a substantially cylindrical stationary magnetic made of ceramic, neodymium, or any other suitable metallic material. The magnet 412 can include an interior lumen extending therethrough along the long axis of the drive assembly 106.

In some examples, a magnetic shield can extend at least partially circumferentially around the upper housing 402. The magnetic shield can take the form of stainless steel or other suitable material configured to shield the magnet 412 disposed within the upper housing 402 from external magnetic interactions. This magnetic shield can ensure that the drive assembly 106 does not actuate in the presence of stray environmental magnetic fields, but rather only initiates movement when the relatively strong magnetic field induced by an external control device is present.

A clutch assembly 408 can be disposed above the magnet 412 and at least partially within the upper housing 402. The clutch assembly 408 includes an upper washer 409, which includes a generally circular base plate coupled to an upwardly extending threaded rod 411, a lower washer 413, and a spring member 415 disposed between the upper washer 409 and the lower washer 413. The lower washer 413 can be in contact on its lower surface with the magnet 412, and optionally can be affixed to the magnet 412 (e.g., via an adhesive, welding, etc.). The threaded rod 411 of the upper washer 409 can be threadably mated with the upper housing 402 (e.g., within the rod 404 of the upper housing 402), such that the upper washer 409 is longitudinally fixed with respect to the upper housing 402 in the absence of rotation. Optionally, the upper end portion of the threaded rod 411 can include an engagement feature (e.g., a detent to receive a flathead screwdriver, or cross-like indentation to receive a Philips head screwdriver, or any other suitable structure) so that a driver can be used to rotate the upper washer 409 relative to the upper housing 402. This rotation can cause the longitudinal position of the upper washer 409 to be adjusted upward and downward. In some implementations, a clinician can make these adjustments after the implant is assembled by removing the locking member 303 from the neck assembly 102, and inserting a driver through the remaining aperture, into the lumen of the rod 404 of the upper housing 402, and into engagement with the upper end of the threaded rod 411 of the upper washer 409.

The spring member 415 can be, for example, a compressible disc-like member, and can be mounted over an upwardly projecting rod coupled to the magnet. The spring member 415 can be a shape-set structure that is biased to expand longitudinally and is compressible to a flattened state as shown. In some examples, the spring member 415 can be a spiral structure surrounding a central aperture.

In operation, when the implant 100 is assembled, the upper washer 409 exerts a downward force on the spring member 415, which in turn exerts a downward force on the lower washer 413. The lower washer 413 interfaces with the magnet 412, such that downward force on the upper washer 409 results in a downward force on the lower washer 413 against the magnet 412. In order to rotate the magnet 412, the rotational force applied to the magnet 412 must be sufficient to overcome the resistance due to the friction between the magnet 412 and the lower washer 413. Accordingly, by increasing the downward force (e.g., via manual rotation of the upper washer 409 to change its longitudinal position relative to the upper housing 402), the frictional resistance to rotation of the magnet 412 can be increased. Depending on the level of frictional resistance, a rotational threshold force is provided, such that the magnet does not rotate in response to forces below the threshold, but does rotate in response to forces above the threshold. This threshold can be adjusted (e.g., by moving the upper washer 409 relative to the housing 402) to a desired value. Such a force threshold can be useful as a safety feature, since the magnet 412 only rotates (and the implant 100 is only lengthened or shortened) in response to sufficiently high rotational force (e.g., due to a sufficiently strong magnetic field). This prevents rotation of the magnet 412 due to incidental or accidental exposure to a magnetic field.

In some embodiments, the magnet 412 can take the form of an outer casing, which can be a hollow generally cylindrical member, and an inner magnetic member, which can be a solid cylinder of neodymium or other magnetic material. In such configurations, inner magnetic member can be friction fit within the outer casing, such that rotation of the inner magnetic member (due to the presence of an external magnetic field) generally causes rotation of the outer casing. However, when the outer casing is firmly held in place (e.g., due to frictional engagement with the lower washer 413), the inner magnetic member may nonetheless rotate within the casing while the casing remains stationary. In this manner, when sufficiently high frictional engagement is achieved between the outer casing and the lower washer 413, the rotation of the inner magnet slips relative to the outer casing, and rotation of the inner magnet does not cause lengthening or shortening of the implant 100.

Optionally, once a desired overall implant length is achieved, the implant 100 can be locked into position, limiting or eliminating the ability for further lengthening or shortening of the implant 100 in response to an external actuation signal. For instance, following a surgical procedure to implant the device and any follow-up adjustments during the recovery process, a clinician may wish to lock in the determined length to prevent any inadvertent adjustments at a later time. In some examples, this can be achieved by increasing the frictional engagement between the lower washer 413 and the magnet 412 to a high level such that even a high applied force does not result in rotation of the magnet 412. To increase the frictional engagement, the upper washer 409 can be lowered (e.g., via manual rotation of the threaded rod 411 using a driver, as noted above) until the spring member 415 is fully compressed and the frictional engagement between the lower washer 413 and the magnet 412 is sufficiently high to prevent any further relative movement. Optionally, an adhesive can be applied to the threaded rod 411 to prevent any further rotation relative to the upper housing 402.

A lower housing 414 is disposed beneath the upper housing 402 (and optionally at least partially surrounded by a magnetic shield). The lower housing 414 can be mated or coupled with the lower housing 414 using any suitable means, including adhesive, threadable engagement, friction fit, etc. The lower housing 414 can include a cavity or interior that receives a portion of the magnet 412 therein, and a downwardly extending rod 418 that engages the gear mechanism 420. In various examples, the lower housing 414 can be glued, friction-fit, or otherwise secured to the magnet 412 such that, when the magnet 412 rotates in response to the magnetic field, the lower housing 414 rotates. In the assembled state, rotation of the magnet 412 causes corresponding rotation of both the upper housing 402 and the lower housing 414. By virtue of the downwardly extending rod 418, which engages the gear mechanism 420, rotation of the lower housing 414 also causes rotation of the internal gears within the gear mechanism 420.

The gear mechanism 420 can take any suitable form configured to step down a first degree of rotational movement of the magnet 412 to a second, lower degree of rotation of the threaded rod 422. In various embodiments, the gear mechanism 420 can include one or more planetary gears.

A lower carrier 424 is disposed beneath the gear mechanism 420, and can support the gear mechanism 420. The lower carrier 424 can include a plurality of upwardly extending rods or other members configured to securely engage the gear mechanism 420 such that the carrier 424 is rotated by rotation of the gears within the gear mechanism 420. The lower carrier 424 also includes a downwardly projecting shaft 428 that is configured to couple with the interior of the threaded rod 422. A thrust bearing 432, seal 434, and retaining ring 430 can each be slidably disposed over the downwardly extending shaft 428. In operation, the seal 434 can prevent ingress of fluids into the other components of the drive assembly 106.

Figure 6A:
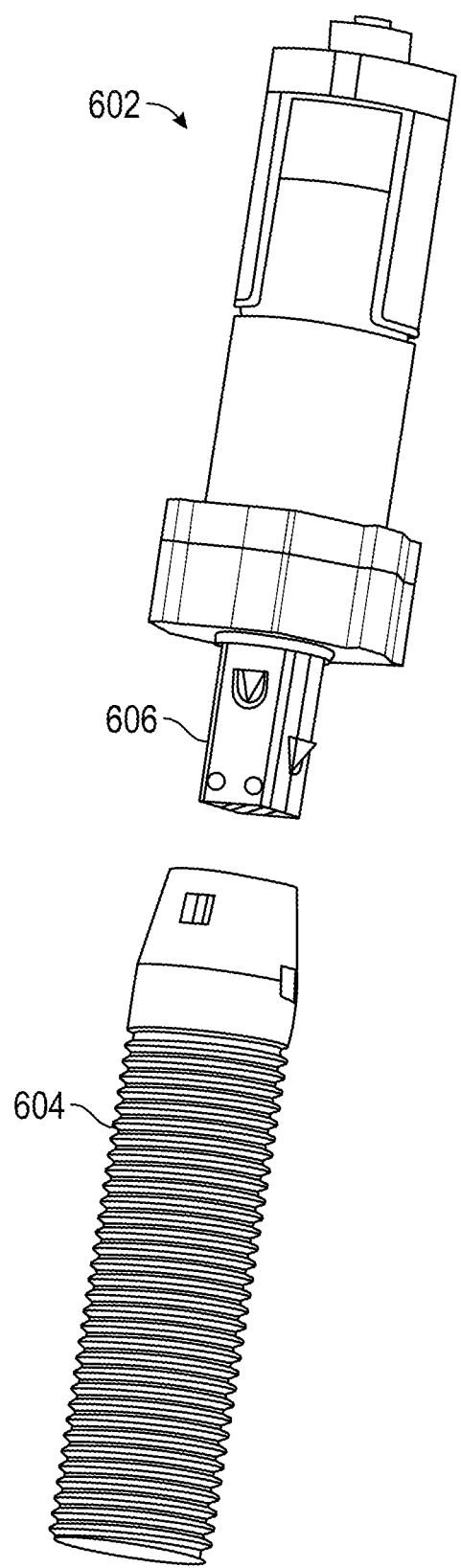
FIG. 6A illustrates a side perspective view of another embodiment of a drive assembly of an orthopedic implant.
Figure 6B:
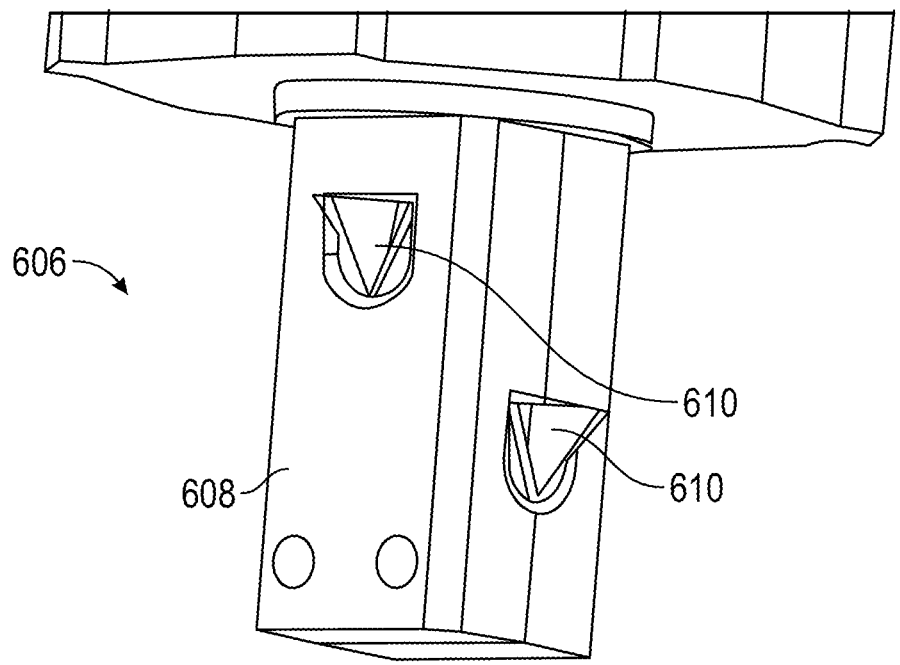
FIG. 6B illustrates an enlarged detail view of a coupling portion of the drive assembly shown in FIG. 6A.
Figure 6B:
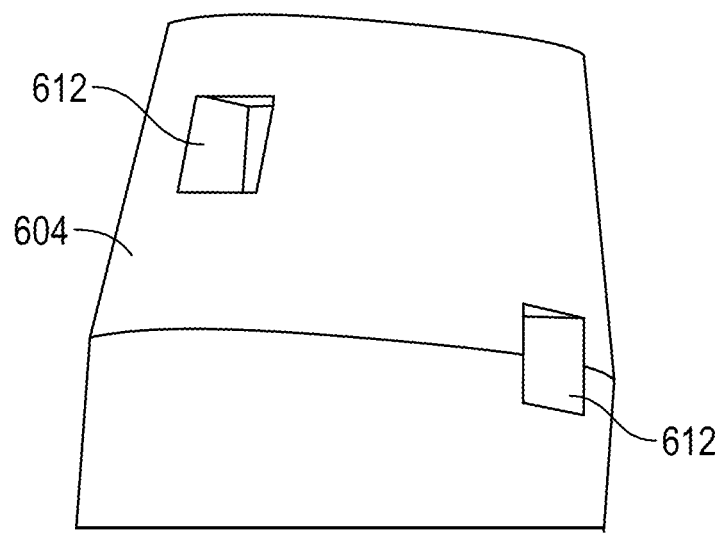

FIG. 6A illustrates a side perspective view of another embodiment of a drive assembly 602. FIG. 6B illustrates an enlarged detail view of the coupling portion of the drive assembly 602. With reference to FIG. 6A and FIG. 6B together, the drive assembly 602 can include several of the features of the drive assembly 106 described above. However, as shown in FIGS. 6A and 6B, the upper portion of the threaded shaft 604 can be configured to engage with the upper portion of the drive assembly 602 via a coupler 606. In particular, the coupler 606 can include a body 608 configured to be received within a lumen of the threaded shaft 604, as well as latches 610 configured to temporarily retract within the body 608 when moved downwardly within the lumen of the threaded shaft 604. The latches 610 can be spring-loaded or otherwise biased radially outwardly such that, when the latches 610 are aligned with apertures 612, the latches extend outwardly from the retracted position to an outwardly projecting position. Because the upper surfaces of the latches 610 are flat (as opposed to the sloped lower surfaces), a downward movement of the threaded shaft 604 relative to the coupler 606 will be prohibited, thereby securely engaging the threaded shaft 604 to the coupler 606.

Figure 7A:
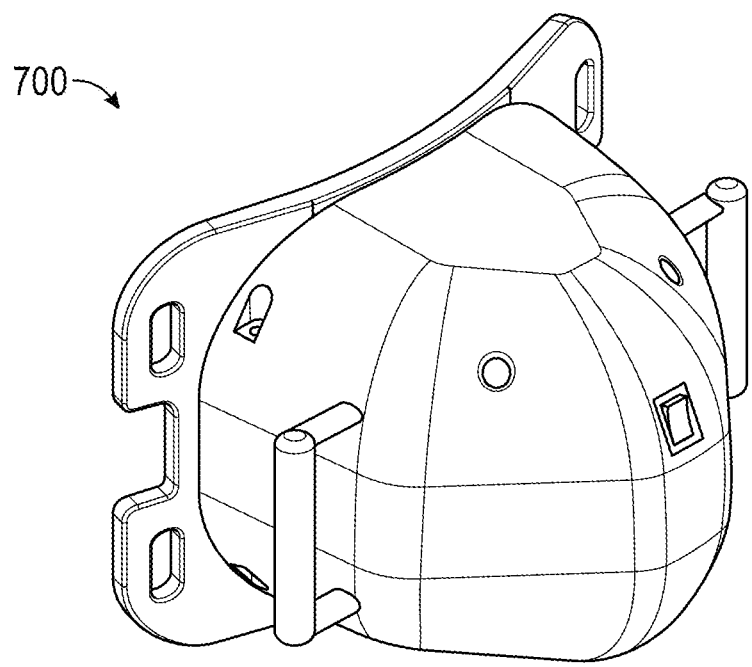
FIG. 7A illustrates a perspective view of an external control device in accordance with one embodiment.
Figure 7B:
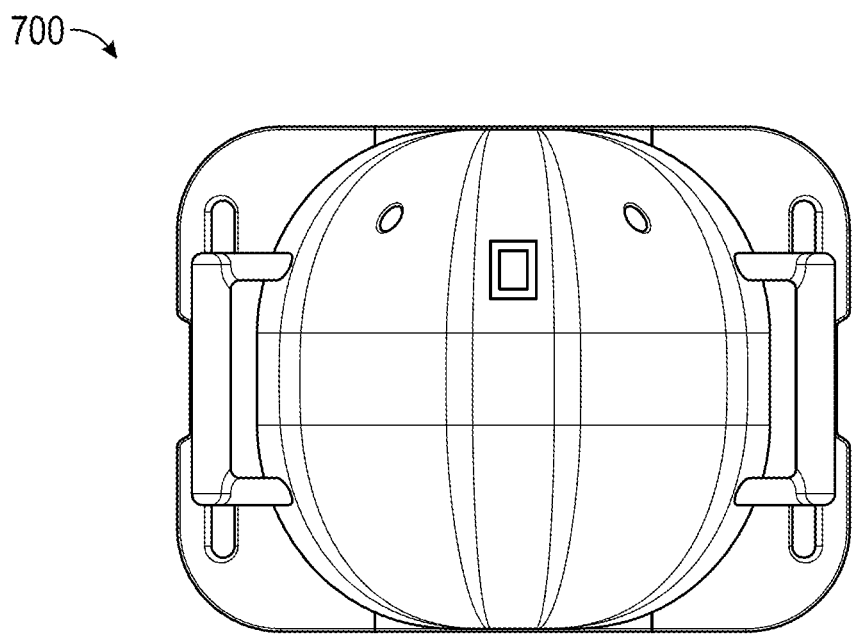
FIG. 7B illustrates a rear view of the external control device shown in FIG. 7B.
Figure 7C:
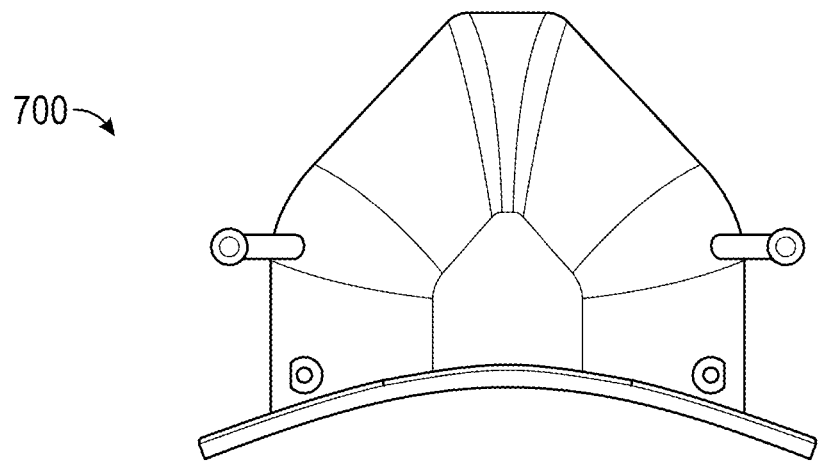
FIG. 7C illustrates a top view of the external control device shown in FIG. 7B.
Figure 7D:
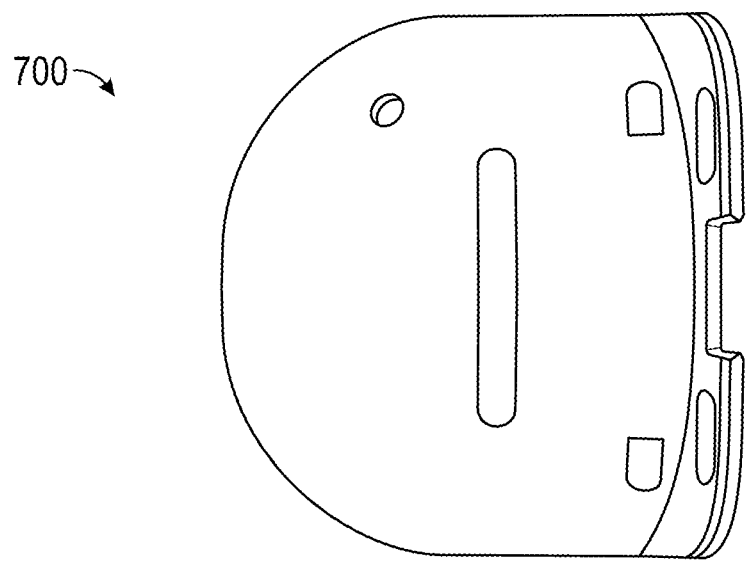
FIG. 7D illustrates a side view of the external control device shown in FIG. 7B.
Figure 8A:
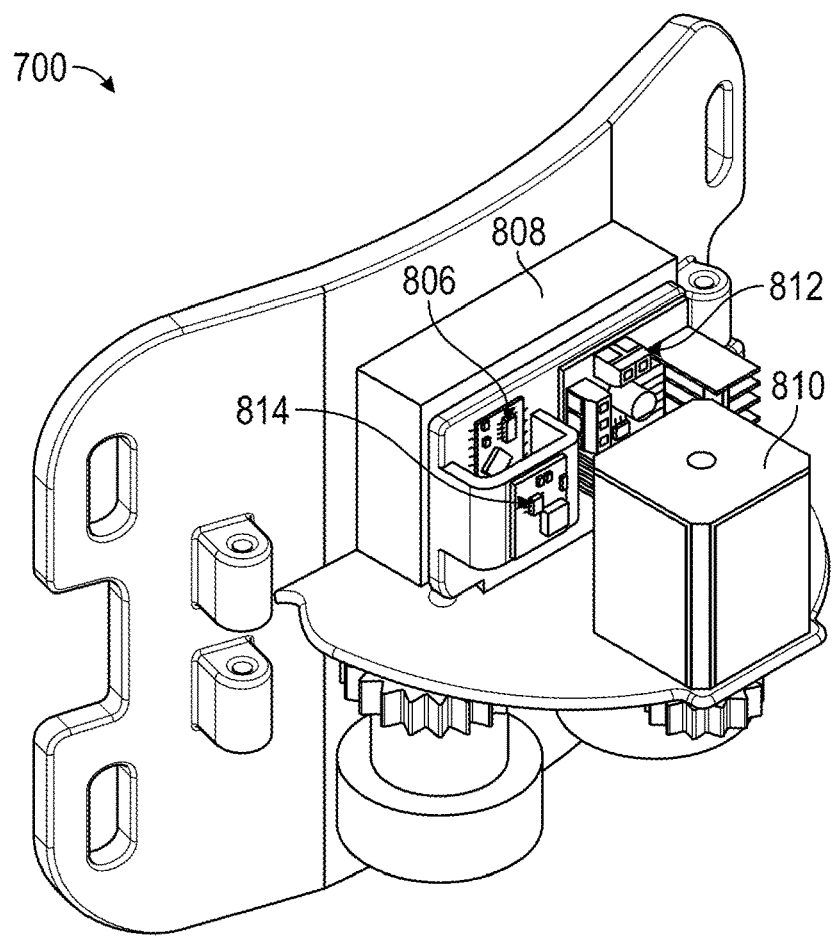
FIG. 8A illustrates a rear perspective view of the external control device with the outer housing omitted for clarity in accordance with one embodiment.
Figure 8B:
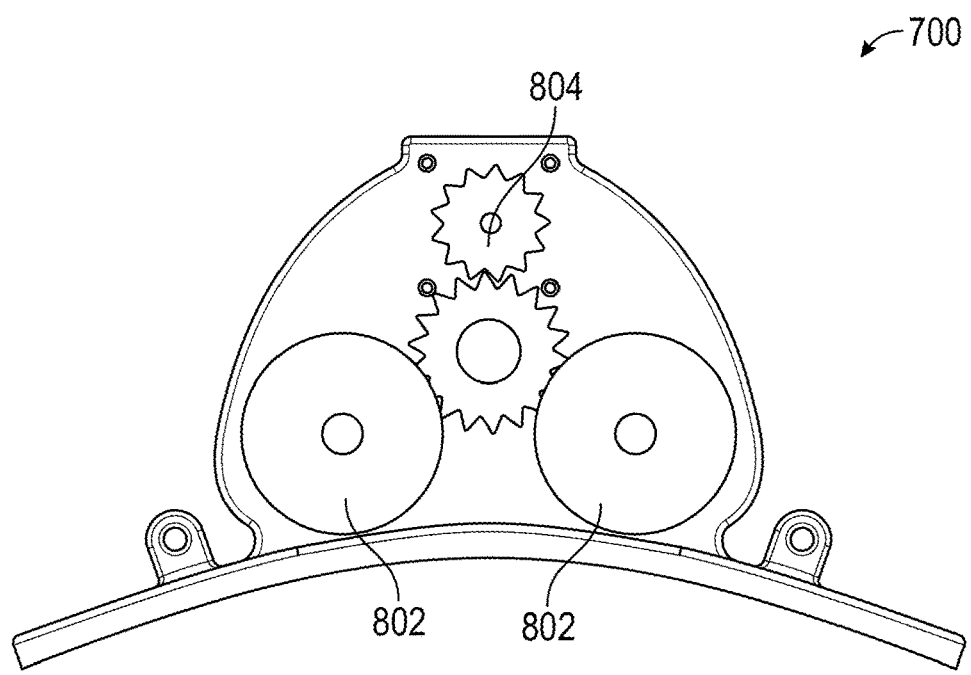
FIG. 8B illustrates a top view of the external control device shown in FIG. 8A.

FIG. 7A is a perspective view of an external control device 700 in accordance with embodiments of the present technology. FIGS. 7B-7D illustrate rear, top, and side views, respectively, of the control device 700. FIG. 8A illustrates a perspective view of the external control device 700 with an external housing omitted for clarity, and FIG. 8B illustrates a top view of the external control device 700 with the external housing omitted. With reference to FIG. 7A to FIG. 8B together, the external control device 700 can include a housing defining a front surface configured to be placed adjacent a patient's body. The front surface can have a contour suitable to the particular body region to which it is to be placed (e.g., a concave surface configured to be placed against a patient's hip). The external control device 700 may be handheld by a clinician and activated via a switch, lever, button, or other such mechanism to initiate generation of a suitable magnetic field to cause the internal magnet of the drive assembly 106 to rotate. In the illustrated embodiment, the external control device 700 includes two neodymium magnets 802 that are rotated by transmission gears 804. In operation, rotation of these magnets 802 can generate a changing magnetic field in the area adjacent the external control device 700. Rotation of the gears 804 and other functions can be controlled via associated electronics (e.g., a control unit 806, battery 808, motor 810, motor driver 812, and DC-DC regulator 814).

In other implementations, any other suitable device or technique can be used to generate a magnetic field (or other such actuation signal) configured to cause the implant 100 to increase or decrease its overall length.

CONCLUSION

Although many of the embodiments are described above with respect to systems, devices, and methods for orthopedic prosthesis, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-8B.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded.

To the extent any materials incorporated herein by reference conflict with the present disclosure, the present disclosure controls.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The present technology is illustrated, for example, according to various aspects described below. Various examples of aspects of the present technology are described as numbered examples for convenience. These are provided as examples and do not limit the present technology. It is noted that any of the dependent examples may be combined in any combination, and placed into a respective independent example. The other examples can be presented in a similar manner.

Example 1. An adjustable orthopedic implant comprising: a neck assembly configured to receive a prosthetic ball thereon for operation in a joint of a patient; a stem assembly configured to be inserted into a medullary canal of a bone of the patient, the stem assembly comprising a cavity having a threaded receptacle therein, the stem assembly being coupleable to the neck assembly; and a drive assembly having a first portion coupled to the neck assembly and a second portion coupled to the stem assembly, the drive assembly configured to vary a relative positioning of the neck assembly and the stem assembly in response to an actuation signal, the drive assembly comprising: an actuator configured to rotate in response to the actuation signal; and a threaded rod coupled to the actuator and configured to rotate in response to rotation of the actuator, wherein the threaded rod is configured to threadably engage the threaded receptacle of the stem assembly such that rotation of the threaded rod in a first direction urges the neck assembly and the stem assembly closer together, and rotation of the threaded rod in a second, opposite direction urges the neck assembly and the stem assembly further apart.

Example 2. The adjustable orthopedic implant of any one of the Examples herein, wherein the drive assembly further comprises a clutch assembly configured to permit rotation of the threaded rod only when a rotational force applied to the actuator exceeds a predetermined threshold.

Example 3. The adjustable orthopedic implant of any one of the Examples herein, wherein the actuator comprises a rotatable magnet coupled to the threaded rod, and wherein the predetermined threshold is adjustable by increasing or decreasing frictional engagement between the clutch assembly and the rotatable magnet.

Example 4. The adjustable orthopedic implant of any one of the Examples herein, wherein the neck assembly comprises an aperture, and wherein the frictional engagement between the clutch assembly and the rotatable magnet can be manually adjusted by accessing the clutch assembly through the aperture.

Example 5. The adjustable orthopedic implant of any one of the Examples herein, further comprising a locking member removably disposed within the aperture of the neck assembly.

Example 6. The adjustable orthopedic implant of any one of the Examples herein, wherein the actuator is coupled to the threaded rod via a gear mechanism that relates a first degree of rotation via the actuator to a second, lesser degree of rotation of the threaded rod.

Example 7. The adjustable orthopedic implant of any one of the Examples herein, wherein the actuator comprises a rotatable magnet, and wherein the actuation signal comprises a magnetic field induced by an external control device.

Example 8. The adjustable orthopedic implant of any one of the Examples herein, wherein the magnetic field can be induced via the external control device with the external control device positioned between about 2-10 inches away from the actuator.

Example 9. The adjustable orthopedic implant of any one of the Examples herein, wherein the stem assembly comprises an outer shell portion having a porous structure to promote osseointegration.

Example 10. The adjustable orthopedic implant of any one of the Examples herein, wherein at least outer shell portion is formed via 3D printing.

Example 11. The adjustable orthopedic implant of any one of the Examples herein, further comprising a magnetic shield disposed at least partially circumferentially around the actuator.

Example 12. The adjustable orthopedic implant of any one of the Examples herein, wherein the magnetic shield comprises stainless steel.

Example 13. The adjustable orthopedic implant of any one of the Examples herein, further comprising a latching mechanism configured to secure the threaded rod to other components of the drive assembly.

Example 14. The adjustable orthopedic implant of any one of the Examples herein, wherein the implant comprises an implantable hip prosthesis, such that the neck assembly is configured to receive a femoral head prosthesis thereon.

Example 16. The adjustable orthopedic implant of any one of the Examples herein, wherein the implant comprises an implantable shoulder prosthesis, such that the neck assembly is configured to receive a humeral head prosthesis thereon.

Example 17. The adjustable orthopedic implant of any one of the Examples herein, wherein the stem assembly is configured to cooperate with a plurality of different-sized head assemblies.

Example 18. The adjustable orthopedic implant of any one of the Examples herein, wherein the drive assembly further comprises a seal member surrounding the threaded rod to preclude the entry of bodily fluid into an internal chamber of the drive assembly.

Example 19. An adjustable orthopedic implant comprising: a first component; a second component configured to be coupled to the first component; and a drive assembly having a first portion coupled to the first component and a second portion coupled to the second component, the drive assembly configured to vary a relative positioning of the first component and the second component in response to an actuation signal, the drive assembly comprising: an actuator configured to rotate in response to the actuation signal; and a threaded rod coupled to the actuator and configured to rotate in response to rotation of the actuator, wherein the threaded rod is configured to threadably engage a threaded receptacle of the second component such that rotation of the threaded rod changes a relative position of the first component and the second component.

Example 20. The adjustable orthopedic implant of any one of the Examples herein, wherein the first component comprises a neck assembly and the second component comprises a stem assembly.

Example 21. The adjustable orthopedic implant of any one of the Examples herein, wherein the drive assembly further comprises a clutch assembly configured to permit rotation of the threaded rod only when a rotational force applied to the actuator exceeds a predetermined threshold.

Example 22. A method of inserting an orthopedic implant comprising: disposing a stem assembly of an implant into a medullary cavity of a patient; coupling a neck assembly of the implant to the neck assembly of the implant such that a drive assembly has a first portion at least partially received within the neck assembly and a second portion at least partially received within the stem assembly, the drive assembly comprising: an actuator configured to rotate in response to an actuation signal; and a threaded rod coupled to the actuator and configured to rotate in response to rotation of the actuator, wherein the threaded rod threadably engages a threaded receptacle of the stem assembly; providing the actuation signal to the actuator to cause the actuator to rotate, thereby rotating the threaded rod with respect to the threaded receptacle and moving the stem assembly and the neck assembly further apart or closer together.

Example 23. The method of any one of the Examples herein, wherein disposing the stem assembly comprises hammering the stem assembly into the medullary cavity of the patient prior to coupling the neck assembly to the stem assembly.

Example 24. The method of any one of the Examples herein, wherein coupling the stem assembly to the neck assembly comprises threading the threaded rod of the drive assembly into the threaded receptacle of the stem assembly.

Example 25. The method of any one of the Examples herein, wherein providing the actuation signal comprises generating a magnetic field via an external control device.

Example 26. The method of any one of the Examples herein, wherein the external control device comprises a housing configured to be placed over a patient's skin at a location adjacent to the implant.

Example 27. The method of any one of the Examples herein, wherein the actuation signal is provided after a surgical procedure to insert the implant into the patient's body.

Example 28. The method of any one of the Examples herein, wherein the drive assembly comprises a clutch assembly, the method further comprising adjusting a force threshold of the actuator by increasing frictional engagement of the clutch assembly.

The invention claimed is:

1. An adjustable orthopedic implant comprising:
a neck assembly configured to receive a prosthetic ball thereon for operation in a joint of a patient;
a stem assembly configured to be inserted into a medullary canal of a bone of the patient, the stem assembly comprising a cavity having a threaded receptacle therein, the stem assembly being coupleable to the neck assembly; and
a drive assembly having a first portion coupled to the neck assembly and a second portion coupled to the stem assembly, the drive assembly configured to vary a relative positioning of the neck assembly and the stem assembly in response to an actuation signal, the drive assembly comprising:
an actuator configured to rotate in response to the actuation signal;
a threaded rod coupled to the actuator and configured to rotate in response to rotation of the actuator, wherein the threaded rod is configured to threadably engage the threaded receptacle of the stem assembly such that rotation of the threaded rod in a first direction urges the neck assembly and the stem assembly closer together, and rotation of the threaded rod in a second, opposite direction urges the neck assembly and the stem assembly further apart; and
a clutch assembly configured to permit rotation of the threaded rod only when a rotational force applied to the actuator exceeds a predetermined threshold, the predetermined threshold being adjustable, wherein the actuator comprises a rotatable magnet coupled to the threaded rod, and wherein the predetermined threshold is adjustable by increasing or decreasing frictional engagement between the clutch assembly and the rotatable magnet.

2. The adjustable orthopedic implant of claim 1, wherein the neck assembly comprises an aperture, and wherein the frictional engagement between the clutch assembly and the rotatable magnet can be manually adjusted by accessing the clutch assembly through the aperture.

3. The adjustable orthopedic implant of claim 2, further comprising a locking member removably disposed within the aperture of the neck assembly.

4. The adjustable orthopedic implant of claim 1, wherein the actuator is coupled to the threaded rod via a gear mechanism that relates a first degree of rotation via the actuator to a second, lesser degree of rotation of the threaded rod.

5. The adjustable orthopedic implant of claim 1, wherein the actuator comprises a rotatable magnet, and wherein the actuation signal comprises a magnetic field induced by an external control device.

6. The adjustable orthopedic implant of claim 1, wherein the stem assembly comprises an outer shell portion having a porous structure to promote osseointegration.

7. The adjustable orthopedic implant of claim 1, further comprising a magnetic shield disposed at least partially circumferentially around the actuator.

8. The adjustable orthopedic implant of claim 1, further comprising a latching mechanism configured to secure the threaded rod to other components of the drive assembly.

9. The adjustable orthopedic implant of claim 1, wherein the implant comprises an implantable hip prosthesis, such that the neck assembly is configured to receive a femoral head prosthesis thereon.

10. The adjustable orthopedic implant of claim 1, wherein the implant comprises an implantable shoulder prosthesis, such that the neck assembly is configured to receive a humeral head prosthesis thereon.

11. An adjustable orthopedic implant comprising:
a first component;
a second component configured to be coupled to the first component; and
a drive assembly having a first portion coupled to the first component and a second portion coupled to the second component, the drive assembly configured to vary a relative positioning of the first component and the second component in response to an actuation signal, the drive assembly comprising:
an actuator configured to rotate in response to the actuation signal;
a threaded rod coupled to the actuator and configured to rotate in response to rotation of the actuator, wherein the threaded rod is configured to threadably engage a threaded receptacle of the second component such that rotation of the threaded rod changes a relative position of the first component and the second component; and
a clutch assembly configured to permit rotation of the threaded rod only when a rotational force applied to the actuator exceeds a predetermined threshold, wherein the predetermined threshold is adjustable by increasing or decreasing frictional engagement of the clutch assembly.

12. A method of inserting an orthopedic implant comprising:
disposing a stem assembly of an implant into a medullary cavity of a patient;
coupling a neck assembly of the implant to the stem assembly of the implant such that a drive assembly has a first portion at least partially received within the neck assembly and a second portion at least partially received within the stem assembly, the drive assembly comprising:
an actuator configured to rotate in response to an actuation signal;
a clutch assembly; and
a threaded rod coupled to the actuator and configured to rotate in response to rotation of the actuator, wherein the threaded rod threadably engages a threaded receptacle of the stem assembly;
providing the actuation signal to the actuator to cause the actuator to rotate, thereby rotating the threaded rod with respect to the threaded receptacle and moving the stem assembly and the neck assembly further apart or closer together; and adjusting a force threshold of the actuator by increasing frictional engagement of the clutch assembly.

13. The method of claim 12, wherein disposing the stem assembly comprises hammering the stem assembly into the medullary cavity of the patient prior to coupling the neck assembly to the stem assembly.

14. The method of claim 12, wherein coupling the stem assembly to the neck assembly comprises threading the threaded rod of the drive assembly into the threaded receptacle of the stem assembly.

15. The method of claim 12, wherein providing the actuation signal comprises generating a magnetic field via an external control device.

16. The method of claim 12, wherein the actuation signal is provided after a surgical procedure to insert the implant into the patient's body.

\* \* \* \* \*